US00PP33829P2

(12) United States Plant Patent
Beekenkamp

(10) Patent No.: US PP33,829 P2
(45) Date of Patent: Jan. 4, 2022

(54) ***BEGONIA* PLANT NAMED 'BKPBERP'**

(50) Latin Name: ***Begonia* x *hiemalis***
Varietal Denomination: BKPBERP

(71) Applicant: Annie Cornelia Beekenkamp, Maasdijk (NL)

(72) Inventor: Annie Cornelia Beekenkamp, Maasdijk (NL)

(73) Assignee: Beekenkamp Plants B.V., Maasdijk (NL)

( * ) Notice: Subject to any disclaimer, the term of this patent is extended or adjusted under 35 U.S.C. 154(b) by 0 days.

(21) Appl. No.: 17/183,023

(22) Filed: Feb. 23, 2021

(51) Int. Cl.
*A01H 5/02* (2018.01)
*A01H 6/18* (2018.01)

(52) U.S. Cl.
USPC ..... Plt./349

(58) Field of Classification Search
USPC ..... Plt./349, 343, 344, 348
CPC ... A01H 5/02; A01H 5/00; A01H 6/18; A01H 6/185; A01H 1/107; A01H 1/121
See application file for complete search history.

*Primary Examiner* — June Hwu
(74) *Attorney, Agent, or Firm* — C. Anne Whealy

(57) ABSTRACT

A new and distinct cultivar of *Begonia* plant named 'BKPBERP', characterized by its compact, broadly upright and mounded plant habit; sturdy plants with freely basal branching habit; dark green-colored leaves; uniform and freely flowering habit; and double-type flowers that are purplish red/pink in color.

2 Drawing Sheets

Figure 1:
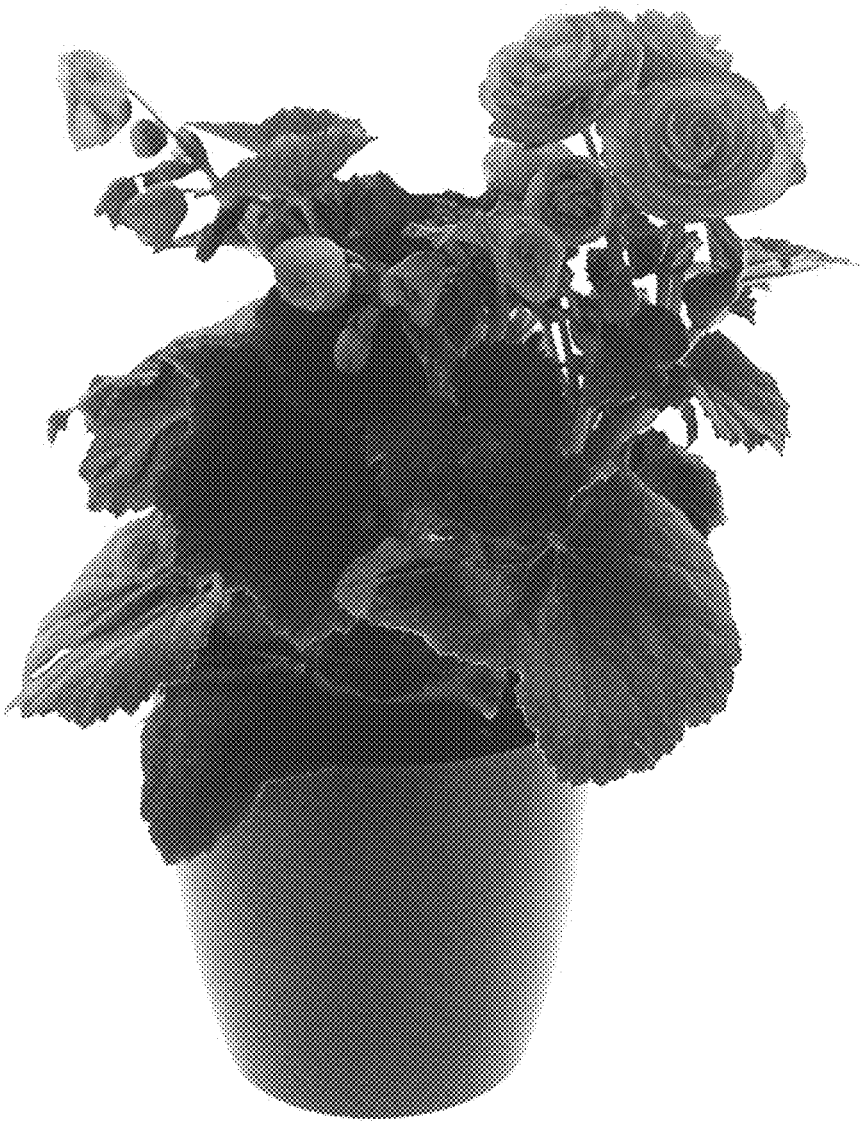

Botanical designation: *Begonia* x *hiemalis*.
Cultivar denomination: 'BKPBERP'.

STATEMENT REGARDING PRIOR DISCLOSURES BY THE INVENTOR/APPLICANT & ASSIGNEE

An European Community Plant Breeder's Rights application for the instant plant was filed by the Assignee, Beekenkamp Plants B.V. of Maasdijk, The Netherlands on Sep. 25, 2020, application number 2020/2347. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Begonia* plant, botanically known as *Begonia* x *hiemalis*, commercially referred to as Elatior Begonia and hereinafter referred to by the name 'BKPBERP'.

The new *Begonia* plant is a product of a planned breeding program conducted by the Inventor in Maasdijk, The Netherlands. The objective of the breeding program was to develop new compact, freely branching and freely flowering *Begonia* plants with attractive flowers and good garden performance.

The new *Begonia* plant is a naturally-occurring whole plant mutation of *Begonia* x *hiemalis* 'BKPBEEFR', disclosed in U.S. Plant Pat. No. 28,684. The new *Begonia* plant was discovered and selected by the Inventor as a single flowering plant from within a population of plants of 'BKPBEEFR' in a controlled greenhouse environment in Maasdijk, The Netherlands in April, 2015.

Asexual reproduction of the new *Begonia* plant by vegetative tip cuttings in a controlled greenhouse environment in Maasdijk, The Netherlands since June, 2015 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'BKPBERP'. These characteristics in combination distinguish 'BKPBERP' as a new and distinct *Begonia* plant:

1. Compact, broadly upright and mounded plant habit.
2. Sturdy plants with freely basal branching habit.
3. Dark green-colored leaves.
4. Uniform and freely flowering habit.
5. Double-type flowers that are purplish red/pink in color.

Plants of the new *Begonia* can be compared to plants of the mutation parent, 'BKPBEEFR'. Plants of the new *Begonia* differ primarily from plants of 'BKPBEEFR' in the following characteristics:

1. Plants of the new *Begonia* are more compact than and not as open as plants of 'BKPBEEFR'.
2. Plants of the new *Begonia* have purplish red/pink-colored flowers whereas plants of 'BKPBEEFR' have duller pink-colored flowers.

Plants of the new *Begonia* can be compared to plants of *Begonia* x *hiemalis* 'Elektra Pink', disclosed in U.S. Plant Pat. No. 18,967. Plants of the new *Begonia* differ primarily from plants of 'Elektra Pink' in plant habit as plants of the new *Begonia* are more mounding than and not as upright as plants of 'Elektra Pink'.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet (FIG. 1) comprises a side perspective view of a typical flowering plant of 'BKPBERP' grown in a container.

Figure 2:
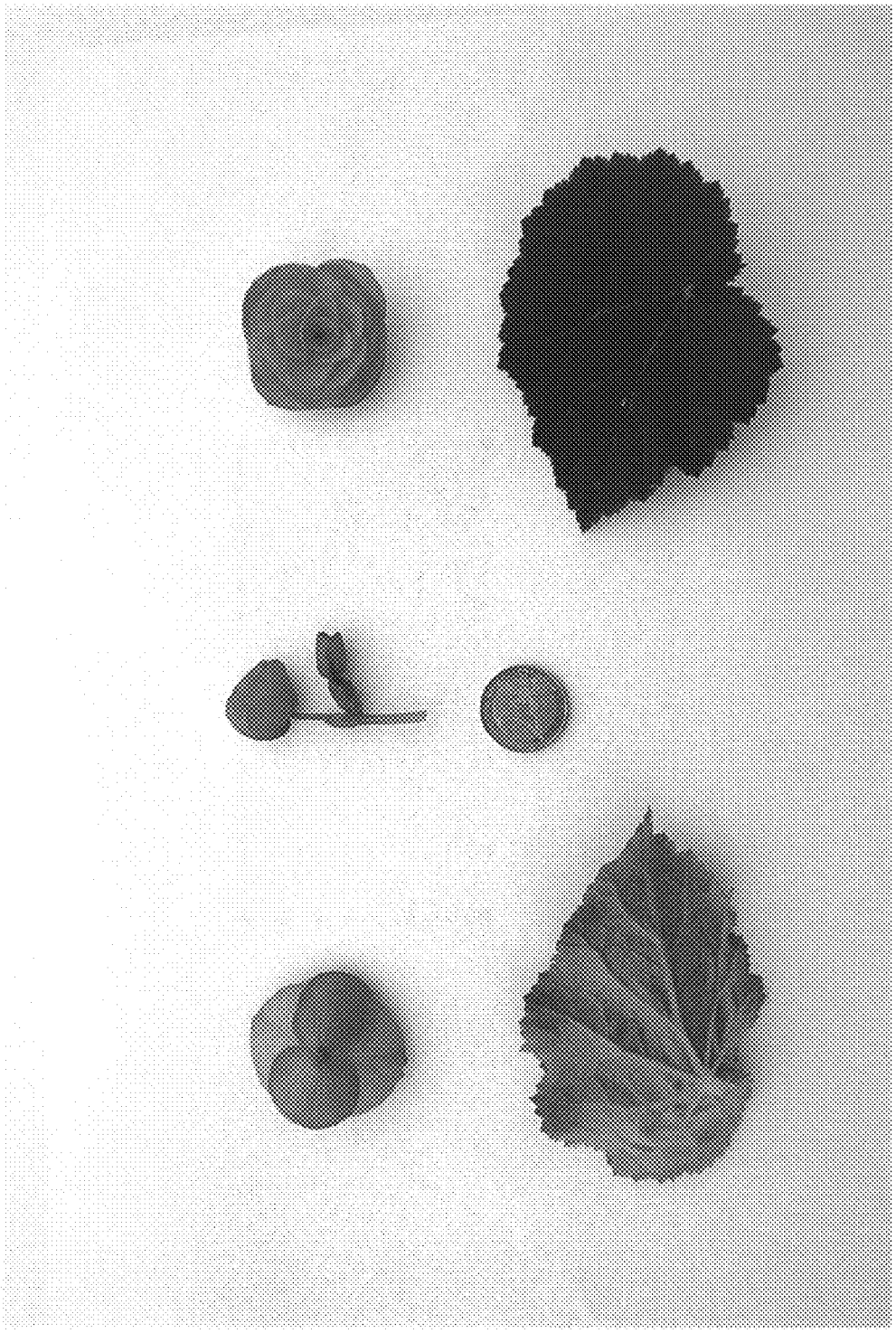

The photograph on the second sheet (FIG. 2) are close-up views of a typical flower bud and the upper and lower surfaces of typical developed flowers and leaves of 'BKPBERP'.

DETAILED BOTANICAL DESCRIPTION

Plants used for the aforementioned photographs and following observations and measurements were grown during the autumn in 10.5-cm containers in a glass-covered greenhouse in Maasdijk, The Netherlands. During the production of the plants, day and night temperatures ranged from 19° to 21° C. Plants were eleven weeks from planting rooted cuttings when the photographs and the description were taken. In the following description, color references are made to The Royal Horticultural Society Colour Chart, 2015 Edition, except where general terms of ordinary dictionary significance are used.

Botanical classification: *Begonia* x *hiemalis* 'BKPBERP'.

Parentage: Naturally-occurring whole plant mutation of *Begonia* x *hiemalis* 'BKPBEEFR', disclosed in U.S. Plant Pat. No. 28,684.

Propagation:

*Type.*—By vegetative tip cuttings.

*Time to initiate roots.*—About 20 days at temperatures about 25° C.

*Time to produce a rooted young plant.*—About 35 to 36 days at temperatures about 21° C. to 23° C.

*Root description.*—Medium in thickness, fibrous; typically light brown in color, actual color of the roots is dependent on substrate composition, water quality, fertilizer type and formulation, substrate temperature and physiological age of roots; plants of the new *Begonia* have not been observed to form tubers.

*Rooting habit.*—Freely branching habit; medium density.

Plant description:

*Plant and growth habit.*—Compact, broadly upright and mounded plant habit; overall plant shape, obovate to narrowly obovate; moderately vigorous growth habit and moderate growth rate.

*Plant height, soil level to top of foliar plane.*—About 16.3 cm.

*Plant height, soil level to top of floral plane.*—About 19.5 cm.

*Plant width.*—About 20.4 cm.

*Lateral branch description.*—Branching habit: Freely branching habit with about two basal branches per plant each with about four secondary branches; pinching is not required. Length: About 8.9 cm. Diameter: About 7.5 mm to 8 mm. Internode length: About 1.8 cm. Strength: Moderately strong. Aspect: Erect to about 40° from vertical. Texture and luster: Sparsely pubescent; moderately glossy. Color, developing: Close to 152B to 152C. Color, fully developed: Close to 146C; surfaces exposed to direct sunlight, slightly tinged with close to 152C.

*Leaf description.*—Arrangement: Alternate, simple. Length: About 10.3 cm. Width: About 8 cm. Shape: Broadly ovate. Apex: Acute to bluntly acute. Base: Oblique, lobes occasionally imbricate. Margin: Crenate to serrate; coarsely undulate. Texture and luster, upper surface: Smooth, glabrous; velvety; very slightly glossy. Texture and luster, lower surface: Mostly smooth and glabrous with sparse pubescence along the veins; velvety; matte. Venation pattern: Pinnate. Color: Developing leaves, upper surface: Close to between NN137A and 139A; margins, strongly tinged with close to 183A. Developing leaves, lower surface: Close to 146B tinged with close to 182C; margins, strongly tinged with close to 184A. Fully expanded leaves, upper surface: Close to between 147A and N189A; venation, close to 147B. Fully expanded leaves, lower surface: Close to 191A tinged with close to 183D; venation, close to 146C. Petioles: Length: About 3.3 cm. Diameter: About 4 mm. Strength: Flexible. Texture and luster, upper and lower surfaces: Sparsely to moderately pubescent; moderately glossy. Color, upper surface: Close to 146B; at distal end, slightly tinged with close to 182B. Color, lower surface: Close to 146C; at distal end, slightly tinged with close to 182B. Stipules: Quantity per leaf: Two at the base of the leaf. Length: About 8 mm. Width: About 8 mm. Shape: Broadly ovate. Apex: Obtuse to broadly acute. Base: Broadly cuneate. Margins: Entire. Color, upper surface: Close to 145A; towards the margins, close to 180D. Color, lower surface: Close to 147C; towards the margins, close to 180C.

Flower description:

*Flowering habit.*—Rotate double-type sterile male flowers arranged in axillary compound cymes; freely flowering habit with about four flowers per cyme and about 200 flowers developing per plant during the flowering season; flowers face upright to outwardly.

*Fragrance.*—None detected.

*Natural flowering season.*—Long flowering period, plants flower freely and continuously from spring into the autumn in The Netherlands; during the winter in a greenhouse, plants begin flowering about 40 days after exposure to photoinductive treatments.

*Postproduction longevity.*—Individual flowers last about ten days on the plant; flowers not persistent; plants maintain good substance for about 20 to 30 days in an interior environment.

*Inflorescence height.*—About 9.3 cm.

*Inflorescence diameter.*—About 6.6 cm.

*Flower buds.*—Length: About 1.4 cm. Diameter, flattened: About 0.9 cm to 1.2 cm. Shape: Obovate; flattened. Texture and luster: Smooth, glabrous; velvety; matte and at the base, very slightly glossy. Color: Close to 181B.

*Flowers.*—Diameter: About 4.5 cm. Depth: About 2 cm. Tepals: Quantity and arrangement: Two per flower, opposite. Length: About 2.4 cm. Width: About 2.3 cm. Shape: Broadly ovate to nearly orbicular. Apex: Rounded. Base: Truncate. Margin: Entire, not undulate. Texture and luster, upper surface: Smooth, glabrous, velvety; matte. Texture and luster, lower surface: Smooth, glabrous, moderately velvety; very slightly glossy. Color: When opening, upper surface: Close to 55B; towards the margins, close to 53D. When opening, lower surface: Close to 51A; towards the base, close to between 179A and 180A. Fully opened, upper surface: Close to between 55B and 63C; towards the margins, close to 63A; venation, close to 185D; color does not fade with development. Fully opened, lower surface: Close to 51A; towards the base, close to 181C; venation, close to 182A; color does not fade with development. Tepaloids: Quantity and arrangement: About 32 arranged in about nine whorls interior to the tepals. Length: About 2.1 cm, varying between 1.4 cm and 2.7 cm. Width: About 2 cm, varying between 1.2 cm and 3.3 cm. Shape: Reniform to obovate. Apex: Obtuse to rounded. Base: Truncate to cuneate. Margin: Entire, not undulate. Texture and luster, upper surface: Smooth, glabrous, velvety; matte. Texture and luster, lower surface: Smooth, glabrous, moderately velvety; matte. Color: When opening, upper surface: Close to 63B; towards the margins, close to 58C. When opening, lower surface: Close to 64D; towards the margins, close to 58C. Fully opened, upper and lower surfaces: Close to between 63B and 63C; towards the margins, close to 63B; venation, close to 185D; color does not fade with development.

*Peduncles.*—Length: About 4.1 cm. Diameter: About 3.5 mm to 4 mm. Angle: About 45° from lateral branch axis. Strength: Moderately strong; flexible. Texture and luster: Smooth, glabrous to sparsely pubescent; moderately glossy. Color: Close to between 152A and 199A.

*Pedicels.*—Length: About 3 cm. Diameter: About 2.5 mm. Angle: About 30° from the peduncle axis. Strength: Moderately strong; flexible. Texture and luster: Moderately pubescent; moderately glossy. Color: Close to 176A.

*Flower bracts.*—Quantity and arrangement: Two per flower, opposite. Length: About 1 cm. Width: About 1.2 cm. Shape: Reniform. Apex: Obtuse to broadly praemorse. Base: Broadly cuneate. Margin: Finely ciliate. Texture and luster, upper and lower surfaces: Smooth, glabrous; very slightly glossy. Color, upper surface: Close to 180B; towards the base, close to 146D. Color, lower surface: Close to 182A; towards the base, close to 147B.

*Reproductive organs.*—None observed, all structures transformed into tepaloids.

*Seeds and fruits.*—Seed and fruit development have not been observed on plants of the new *Begonia* as flowers are sterile.

Pathogen & pest resistance: Resistance to pathogens and pests common to *Begonia* plants has not been observed on plants of the new *Begonia.*

Temperature tolerance: Plants of the new *Begonia* have been observed to tolerate high temperatures of about 35° C. and to be suitable for USDA Hardiness Zones 10 to 12.

It is claimed:

1. A new and distinct *Begonia* plant named 'BKPBERP' as illustrated and described.

* * * * *